United States Patent [19]

Mercado

[11] Patent Number: 5,753,818
[45] Date of Patent: May 19, 1998

[54] METHOD AND APPARATUS FOR MEASURING SCOUR AROUND BRIDGE FOUNDATIONS

[75] Inventor: Edward J. Mercado, Houston, Tex.

[73] Assignee: North American Geotechnical Company, Houston, Tex.

[21] Appl. No.: 665,468

[22] Filed: Jun. 18, 1996

Related U.S. Application Data

[63] Continuation-in-part of Ser. No. 440,821, May 15, 1995, abandoned.

[51] Int. Cl.$^6$ .................... G01M 7/00; G01N 3/30
[52] U.S. Cl. .................... 73/594; 73/597; 73/628
[58] Field of Search .................... 73/584, 594, 597, 73/628, 629, 641

[56] References Cited

U.S. PATENT DOCUMENTS

| | | | |
|---|---|---|---|
| 3,617,996 | 11/1971 | Herbert | 340/3 R |
| 3,641,811 | 2/1972 | Gnaedinger, Jr. et al. | 73/594 |
| 3,690,155 | 9/1972 | Eichler | 73/597 |
| 4,380,930 | 4/1983 | Podhrasky et al. | 73/594 |
| 4,736,630 | 4/1988 | Takahashi et al. | 73/626 |
| 5,297,109 | 3/1994 | Barksdale, Jr. et al. | 367/106 |

FOREIGN PATENT DOCUMENTS

| | | | |
|---|---|---|---|
| 2245736 | 1/1992 | United Kingdom | G08B 21/00 |

*Primary Examiner*—Richard Chilcot
*Assistant Examiner*—Max H. Noori
*Attorney, Agent, or Firm*—Vaden, Eickenroht & Thompson, L.L.P.

[57] ABSTRACT

A method and apparatus for measuring bottom scour adjacent a foundation structure extending into the bottom of a stream of flowing water is disclosed. An elastic wave source is used for transmitting elastic waves through the water, the scour zone, and the bottom adjacent the foundation structure. The elastic waves are transmitted directly to an array of receivers and indirectly through the foundation structure to produce refracted signals that also travel to the receivers. The array of receivers are adapted for substantially vertical positioning such that a portion of the receivers will sense elastic waves that travel through the water above the scour, a portion will sense elastic waves that travel through the scour, and a portion will sense elastic waves that travel through the bottom adjacent the structure. Means are utilized for recording the time required for the elastic waves to reach each receiver to measure the depth of scour next to the foundation structure. The soil profile is deduced by using the known velocities of elastic waves in concrete, water, mud slurries, and soil, as appropriate to determine the amount of scour around the foundation structure.

11 Claims, 7 Drawing Sheets

METHOD AND APPARATUS FOR MEASURING SCOUR AROUND BRIDGE FOUNDATIONS

CROSS-REFERENCE TO RELATED APPLICATION

This patent application is a continuation-in-part to application Ser. No. 08/440,821, filed on May 15, 1995, now abandoned.

BACKGROUND OF THE INVENTION

1. Field of the Invention

This invention relates to measuring scour around bridge foundations and any other structure supported by members that extend into the bottom of a moving body of water.

2. The Related Art

The effect of erosion of the soil bed, or scour, around bridge foundations has long been a consideration in bridge design, both from the point of view of the river hydraulics specialist and from that of the foundation engineer. Numerous bridge failures have been attributed to the undermining of interior piers or abutments by scour during floods. If the depth of scour in the vicinity of a foundation, such as a pier or abutment exceeds the design limits, excessive movements of the foundation can occur, perhaps exceeding the service limit of the structure, even to the extent of completely undermining the foundation and producing collapse of the structure. Collapse from scour unfortunately often results in the loss of life, but always causes serious traffic disruptions and expensive repairs. The Federal Government spends over $50,000,000 annually on the nation's primary road system for emergency bridge repairs, primarily from flood induced scour. Local and state agencies spend over twice that amount annually on emergency repairs to bridges damaged by scour.

A 1988 publication of the Federal Highway Administration cites the following statistics regarding the loss of bridges due to scour: In the spring floods of 1987, 17 bridges in New York and New England were destroyed or damaged by scour, and in 1985, 73 bridges were destroyed by floods in West Virginia, Virginia and Pennsylvania, with damage being distributed approximately equally between piers and abutments. Severe floods in the western U.S. have also produced scour that have destroyed or made unserviceable major highway bridges, an example of which were floods on the Salt River in Arizona in 1988 that completely undermined pile-supported piers.

Considerable serious bridge scour research has been conducted, but most of this research has been confined to the laboratory. This research has resulted in the development of methods, both semi-analytical and empirical, to predict scour depth (e.g., Laursen and Toch, 1953; Liu et al., 1961; Carstens, 1966; Shen et al., 1969, 1970; Richardson et al., 1988), and these equations, among others, are currently used by bridge designers to predict scour depth for foundation design. Most of these methods were developed to apply to a particular type of scour (e.g., local scour at abutments), for particular ranges of Froude numbers in the scouring stream, and for particular foundation configurations and soil characteristics. Predicted scour depths vary according to these procedures, especially when applied outside of the range of parameters for which they were developed.

The acquisition of field data on scour, to augment data acquired from laboratory modeling, has been recognized as being essential to the improvement of the understanding and predictive capabilities regarding the estimation of the depth of scour, configurations of scour zones, and the nature of redeposited soils in the scour zone, if any. Such field studies require appropriate and reliable instrumentation.

The ideal characteristics of scour instrumentation include:

a. The ability to measure scour depth profile, around a footing, drilled shaft, or pile-supported abutment or pier, dynamically. That is, it is desirable to be able to observe the progression of scour depth, infilling, (during the falling stage of the stream) and location of scour zones during a flood in order to understand the full-scale mechanisms involved in the process so that improved predictive models can be developed and scour-susceptible foundations can be identified more accurately;

b. The ability to provide good sediment profile resolution (e.g., to the nearest 6 to 12 inches) in all types of sediments and in waters of varying chemistries (e.g., water carrying a heavy load of clay minerals, salt water, clear fresh water);

C. Either portability or low cost (for fixed installations);

d. Reliability (instrument will not fail under extreme flood and storm conditions); and e. Ease of operation/remote operation (ideally should be operated by state DOT technicians who are not present on the bridge or in the stream during the flood event).

It is therefore an object of this invention to provide instrumentation for measuring scour having all of these characteristics.

The present state of the art is typified by U.S. Pat. Nos. 3,617,996 to Herbert and 5,297,109 to Barksdale et al., which teach the use of electroacoustical transducers to measure scour. Herbert specifically determines the presence of scour by comparing transit times for reflected signals produced by transducers having a common elevation about a bridge pier. Fathometers also make use of reflection mode elastic wave surveying by producing sound waves to sense the solid surface and soil layer interfaces. "Elastic waves" as used herein include acoustic (sound) waves, compressional waves, and shear waves.

The problem with pure reflective mode surveying is that the energy waves travel only through the water above and within the scour zone. Impurities in the water may corrupt the reflected signals so the devices characterized by Herbert are subject to inaccuracies depending on the extent of solids in the water.

It is therefore a further object of this invention to provide a method of and apparatus for measuring scour that use elastic waves but measures the time for the direct and/or refracted elastic waves to reach a substantially vertical array of receivers or sensors that are positioned to receive the waves passing through three distinct media: the water above the scour zone; the muddy water in the scour zone; and the bottom soil beneath the scour. "Receivers" or "sensors" as used herein, include hydrophones, geophones, and accelerometers.

It is a further object to provide such an array of receivers that need not be embedded within the structure of interest during construction, but which can be utilized for scour detection and measurement after the structure has been completed.

It is a further object to provide a method and apparatus that do not depend on knowing a "standard" pulse signature for a scour-free structure, but which identify a scour zone by the anomalous effect the material in the zone has on wave transmission properties when compared systematically with the wave transmissions through the shallow water above the scour zone, through a combination of water-soil medium when the scour zone contains only water, through a water-mud-soil medium when the scour zone contains soft, highly dispersive mud, or through the soil beneath the scour zone.

SUMMARY OF THE INVENTION

The objects described above, as well as other objects and advantages are achieved by a method and apparatus that contemplate the use of an elastic wave source for transmitting elastic waves through the water, the scour zone, and the bottom adjacent a foundation structure. The elastic waves are transmitted directly to an array of receivers and indirectly through the foundation structure to produce refracted signals that also travel to the receivers. The array of receivers are adapted for substantially vertical positioning to sense the elastic waves that pass through the water, the scour zone, and the bottom adjacent the foundation structure. Thus, a portion of the receivers is located in the water above the anticipated scour zone, a portion is located within the depth range of the anticipated scour zone, and a portion is located in the bottom below the anticipated scour zone. Means are utilized for recording the time required for the elastic waves to reach each receiver to measure the depth of scour next to the foundation structure. The soil profile is deduced by using the known velocities of elastic waves in concrete, water, mud slurries, and soil, as appropriate to determine the amount of scour around the foundation structure.

In one embodiment, the elastic waves are transmitted from an elastic wave source positioned atop the foundation structure and the array of receivers is positioned adjacent to but spaced from the foundation structure. The array of receivers may also be positioned in an approximately vertical bore within the foundation structure instead of, or in addition to, the array adjacent the structure.

In another embodiment, the elastic waves are transmitted from an elastic wave source attached to the side of the foundation structure.

In a further embodiment, the elastic waves are transmitted from an elastic wave source positioned in the water adjacent the foundation structure.

BRIEF DESCRIPTION OF THE DRAWINGS

In the drawings, wherein like reference characters are used throughout to describe like parts.

DETAILED DESCRIPTION OF THE PREFERRED EMBODIMENT

Figure 1:
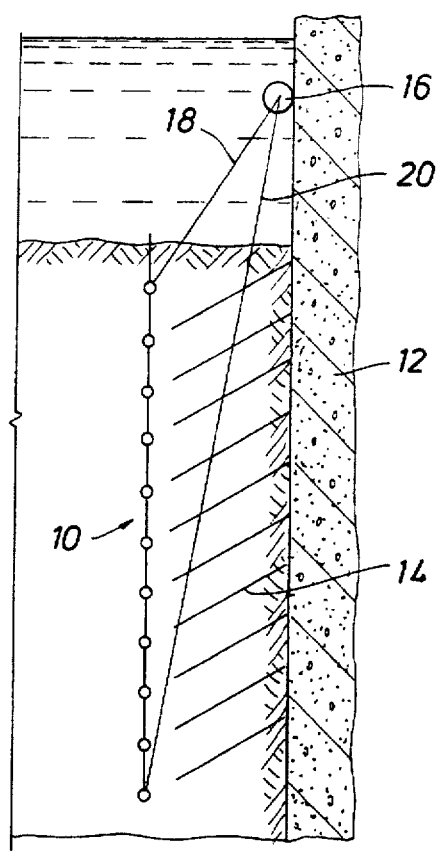
FIG. 1 is a vertical cross-section of a portion of a bridge foundation, a body of water, and the water bottom into which the foundation extends with an approximately vertical array of receivers, shown schematically, extending vertically into the bottom.
Figure 3:
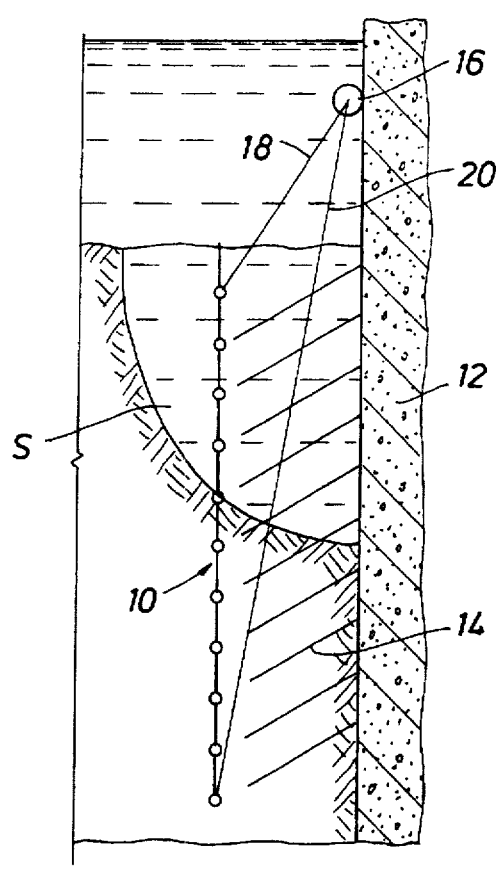
FIG. 3 and FIG. 4 are the same views as FIGS. 1 and 2 except with a scour zone present.

The apparatus (instrument) has both a permanently installed component (the receiver array) and a portable recording component that can be transported from site to site. The receiver array, which would be fixed, but inexpensive, consists of an approximately vertical string of receivers secured within a thin-walled tube shown schematically in FIGS. 1 and 3 and identified by the number 10. The receiver array (or multiple arrays around the foundation or multiple piers) is placed approximately vertically in the stream bed close enough to the pier or abutment 12 being monitored to penetrate the scour zone (if present). By placing the receivers close to the foundation, it receives elastic waves via at least two geometric paths that penetrate the scour zone S (shown in FIG. 3). One path is the refracted energy propagating down the foundation wall and radiating into the soil. This energy is indicated by arrows 14. The second is the elastic wave energy that arrives directly from source 16 placed nearly directly overhead and propagating nearly vertically through the scour zone (if present) to the buried receivers. Two such paths are shown in FIGS. 1 and 3 by lines 18 and 20 that extend from the source to the top and bottom receivers. Elastic wave energy also travels directly to the other receivers.

Seismic data further indicates that the receivers will sense elastic waves via a third path resulting from the refracted energy propagating down the receiver array tube and emanating therefrom where there is a change in the elastic moduli, particularly the shear modulus, along the length of the receiver array tube borehole. This third source of energy is referred to by the inventor as "tube waves," and is believed to be initiated at the interface between the scour zone and the water above the zone, as well as at the interface between the scour zone and the soil below the zone. Consequently, these tube waves may be used to monitor the depth of the scour zone by measuring the onset depth of the waves.

Protecting the top of the receiver array from collision damage with debris is a major concern. Preferably, the array is located within or directly downstream of an H-pile, which can be installed quickly and inexpensively by vibration in most granular sediments, either during initial construction of the foundation or as a part of a scour monitoring program for existing structures. In addition, placing it close to the foundation provides considerable protection.

Figure 10:
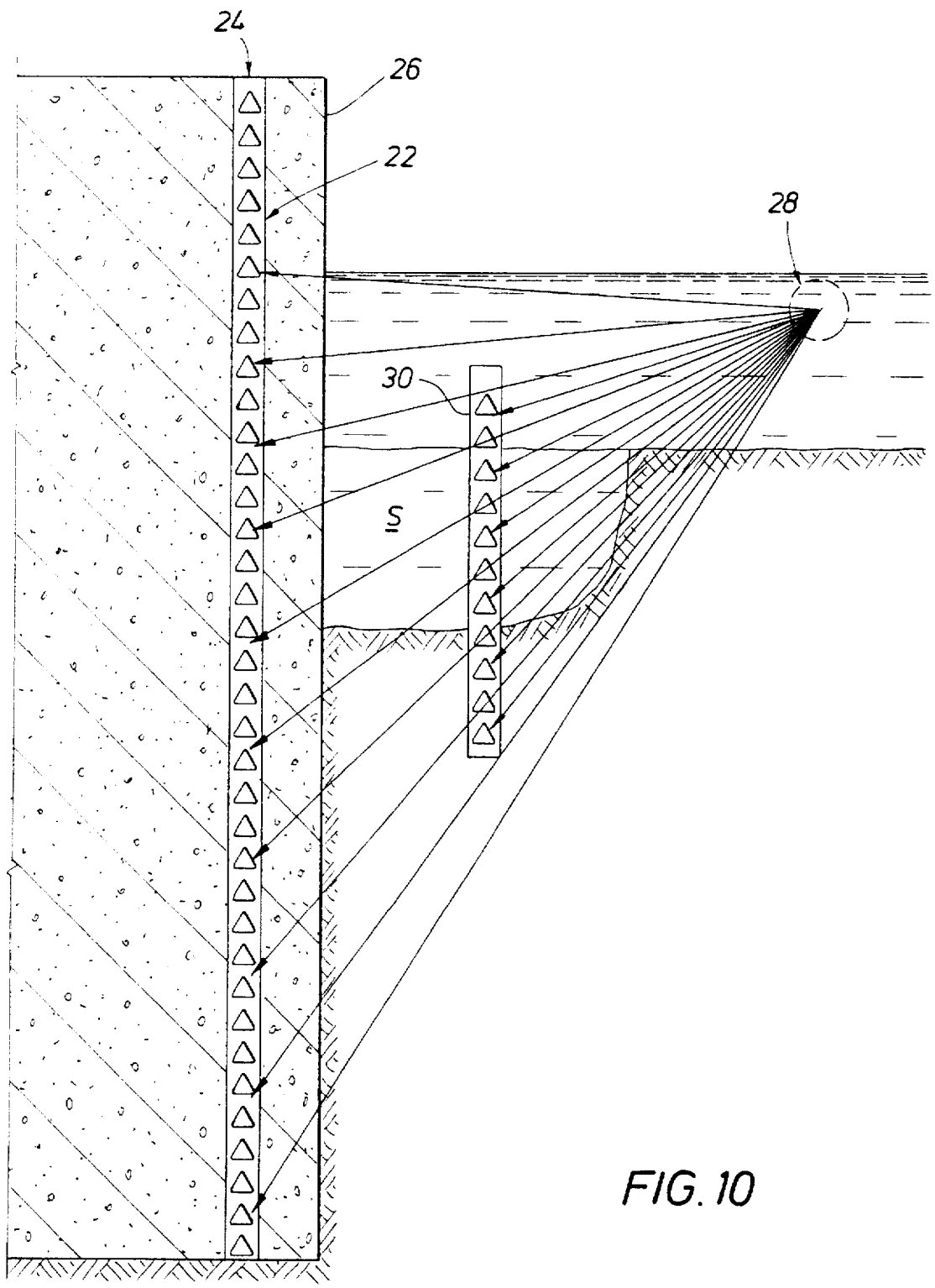
FIG. 10 is a vertical cross-section of a portion of a bridge foundation, such as a concrete pier with two approximately vertical arrays of receivers positioned to measure scour.

In operation, portable energy source 16 is attached to the foundation at a convenient point before or during a flood. Alternatively, the receiver array can be placed in a vertical hole drilled in the bridge foundation as shown in FIG. 10, where receiver array 22 is located in hole 24 in pier 26. With this arrangement the source of energy, shown in FIG. 10 as circle 28, must be positioned for energy from the source to travel through scour zone S as well as the bottom below the scour zone before reaching the receivers so that the difference in the time required for the elastic waves to reach the receivers can be measured.

A second receiver array 30 is shown in FIG. 10. It is adjacent to the pier and extends through the scour zone into the bottom in the path of the elastic waves from source 28. The recordings from either array can be used to measure the depth of scour. But comparing both will give the most accurate indication of the scour depth.

The soundings, i.e., elastic energy pulses, can be repeated continually during a flood event without the need for an on-bridge operator by installing a microcomputer programmed to trigger the seismic pulse generator and the seismic recording system at predetermined intervals. The microcomputer also can be programmed to analyze the data and send a signal to a central site if it detects potentially hazardous conditions.

Some attempts have been made to use multiple-point sound sources and receivers by the U.S. Geological Survey, but they were not found to be easily managed in a river environment (Trent, 1988). Several features of the specific system described here, however, can eliminate the difficulties that have been encountered with similar systems. First, the receiver arrays are installed during quiet river flow periods and remain fixed in position for use as required. Second, the receiver array is protected from water and debris by a shield. Third, noise produced by water turbulence (including the presence of air bubbles in the water) and debris striking the bridge or the H-pile shield can be effectively removed by time-averaging the signal from a large number of pulses produced in rapid succession, since such noise is essentially random. Fourth, with this device, the vertical spacing of the receivers can be varied to provide any degree of resolution required and to read any depth of scour that is required at a particular site. Fifth, accurate records of scour depths and profiles between the foundation and the receiver string can be recorded every few minutes over the course of a flood. The data is stored on a digital tape or floppy disk, which can be retrieved from the seismic recording system as needed during or after the passage of the flood. The recorded data can be analyzed to give a dynamic record of the progression of scour and infilling during or after the flood. Finally, the seismic recorder and controlling microcomputer may be housed in a protective element on the bridge deck or remotely away from the bridge.

The experiment described here has a duration of approximately $1.5 \times [\text{maximum distance traveled}]/V_{concrete}$. For a pulse originating from a gun (an elastic energy source) located approximately three feet above the water bottom and traveling to the deepest transducer approximately thirty feet below the water bottom, the transit time is around four milliseconds. Because the experiment takes place in a time interval very short compared to the rate at which scour is occurring, signal averaging is applicable. The sound source and recorder can be cycled at rates up to two repetitions per second. They also can be operated to sum N successive recordings taken, e.g., ½ second apart over selectable ranges of time. When summed over multiple recordings, the signals traversing the same minimum time path defined by Snell's law will add constructively, while the random, flood generated noise, will combine destructively. This summation will enhance the signal-to-noise ratio by $(N)^{1/2}$, where N is the number of recordings added.

The poorer signal-to-noise environment due to the flood also can be compensated for by increasing the output signal strength. The sound signal power is controllable by varying the operating air pressure used to energize the sound source. Higher pressures produce stronger pulses to combat the higher noise levels present during flood stage.

These techniques of data summing of rapidly repeated soundings and increasing the source output power will overcome the inherent random noise recorded with the desired signals. The resulting data will be dominated by the response of the pier, scour zone, and soil. The repeatable direct arrival and refraction events will be preserved.

The data will be analyzed by two approaches. First, is the analytical approach proposal of identifying the individual events, specifically the refraction arrival, and deducing the soil profile from the known material velocities, and the geometry of the source, receiver, and pier. This same analytical approach may be extended to studying the direct arrival, and again knowing the geometry of the source, the receiver, and the pier, deduce the soil profile from those identified events. Because the direct arrival is so strong relative to the other events, the probability of successfully analyzing it is quite good.

An alternative signal processing technology developed by the geophysics industry has often achieved positive results less directly by analyzing the data for attributes that are directly measurable from the data and are caused by known physical effects. This empirical, or semi-analytical methodology is very useful when the physical phenomena become so complex that analytical methods are inadequate to cope with the data. An example of this approach in the field of reflection seismic data processing is velocity analysis, where a suite of data are repeatedly focused by assuming a set of trial velocity functions that span the range of velocities seen in conventional sedimentary rocks, and measuring the multichannel coherence between these data. The coherence maxima correspond to the correct velocities for the sedimentary section in question, and are identifiable by this process. This semi-analytical technique is well-founded in theory, however, the actual physical situation is so complex, theoretical approaches to analyze the data are impossible.

Both analytical and semi-analytical approaches are valid.

Assume that initially the instrument package was installed adjacent to a pier that has not developed a scour annulus (FIG. 1). The air compressor, recording and control instrument system are remotely located at the surface. The control system sends simultaneous signals to fire the sound source gun and start the multichannel seismic recorder connected to the receiver transducers.

FIGS. 1 and 3 show the direct arrival ray paths and the ray paths of elastic energy traveling down the pier, refracted into the lower velocity soil, and recorded by the receiver array for both the no scour case, FIG. 1 and scour case, FIG. 3.

Figure 2:
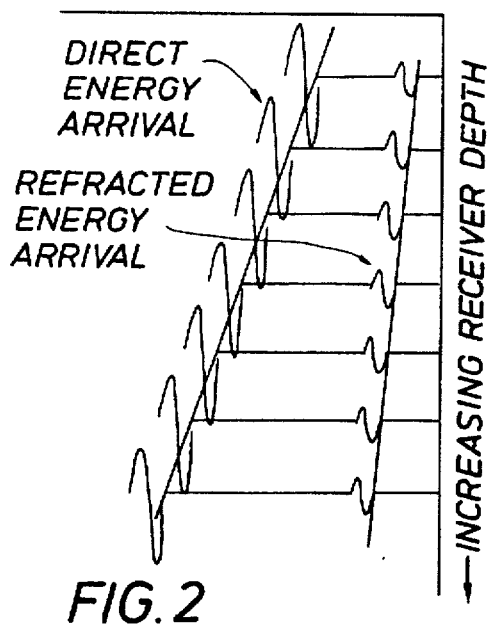
FIG. 2 is a sketch of a recording of the time required for the direct and refracted elastic waves to reach the receivers.

If there is no noise in the system for the no-scour case, the output of the receivers will give a pattern as shown in FIG. 2. The output of each receiver will be quiet until the first energy pulse arrives along the refraction path illustrated in FIG. 2. The first breaks will lie on a straight line with slope $1/V_{concrete}$. After the refraction first breaks, the direct travel energy will be recorded with several times the amplitude of the refraction event. The slope of this event will be $1/V_{soil}$, if the source is directly over the receiver array. A more detailed interval velocity profile of the soil at discrete depths can be inferred from the relative travel times from the source to each of the receivers in the string without having to make any exact measurements of the position of the source on the structure relative to the array, provided the receiver spacing is accurately known. For the vertically traveling direct arrival, the interval velocity is the receiver spacing divided by the incremental travel time between successive receivers. If the source is not directly above the receiver array, the velocity determination is more complex and the arrival time path will follow a hyperbola referred to as the "normal moveout" curve in the exploration geophysics industry. For the refracted arrivals, the velocity is calculated from the arrival time of refraction energy as shown in FIG. 2, knowing the distance separating the array from the pier, and applying an approximate value for the critical angle. Since the velocities of the elastic waves are known in concrete, water, and for various sediments, the profile around the foundation can be inferred from the event arrival patterns.

Figure 4:
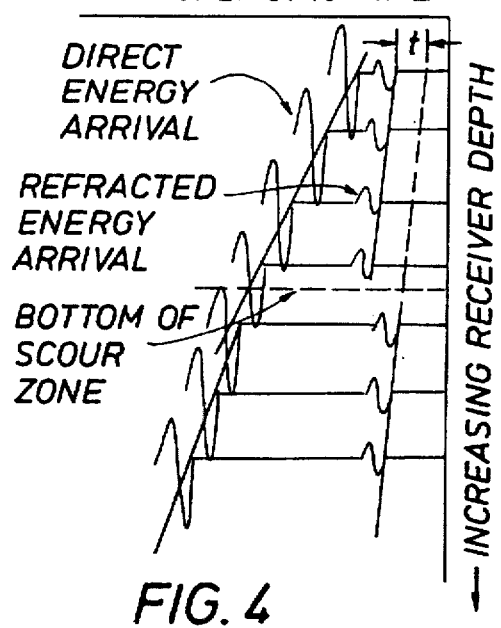

Next, assume that a scour annulus has developed to a depth of approximately five feet around the pier, the eroded soil with sound velocity $V_{soil}$ has been replaced by a mud slurry with lower velocity $V_{slurry}$, as shown in FIG. 3. The scour effect on the recorded pattern of elastic wave arrivals will be seen first at the shallowest receiver and progress to successively deeper receivers. The changed output pattern of the receivers is illustrated in FIG. 4 when the scour depth has reached the top four transducers. Both direct and refracted rays traversing the slurry zone will be delayed due to the slower velocity of the slurry zone, in contrast to the deeper refracted rays that do not penetrate the scoured zone. All the direct travel rays will be delayed due to the slower velocity of the scour infill material, $V_{slurry}$. In addition, a break in the slope of the arrival pattern will develop due to the changed interval velocity measured between successive receivers. This effect also is illustrated in FIG. 4.

Although of lesser interest, the thickness of the scour annulus can be inferred from the delay, $\Delta t$, in the refraction arrival pulse at the shallow receivers relative to the straight line extrapolation of arrival time from the unaffected receivers, as sketched in FIG. 4.

Another point of view is to consider the experiment conducted with the source, receiver, buried pier, no scour zone geometry as shown in FIG. 1. The data from that geometry, with no scour zone present, show relatively smooth change in overall amplitudes from shallowest to deepest receiver in FIG. 2. This variation in recorded power as a function of depth of burial is confirmed by treating the receiver outputs as conventional time series, and calculating this signals rms (root mean square) level, and plotting this energy level as a function of trace number. Because of the recording geometry, trace number is a measure of distance the recorded energy has traveled, regardless of what specific path or mode of propagation the energy traveled by. This rms energy level is shown plotted in FIG. 9 as the curve with the open circles. This energy level is called an "attribute" because it is calculated directly from the data with no unique physical definition. It is smoothly varying, and follows approximately the decay with distance one would expect from energy decaying according to the formulas for spherical spreading of elastic waves, with the exception of the energy level measured at trace 1. The energy at trace 1 is low due to clipping during recording from the fixed point gain amplifiers in the recording system. The laws of physical elastic waves would predict this type of behavior from general physical principals, as the elastic wave field has been generated in a rather homogeneous, two layered media (the pier and the soil), with nothing to perturb it.

Figure 6:
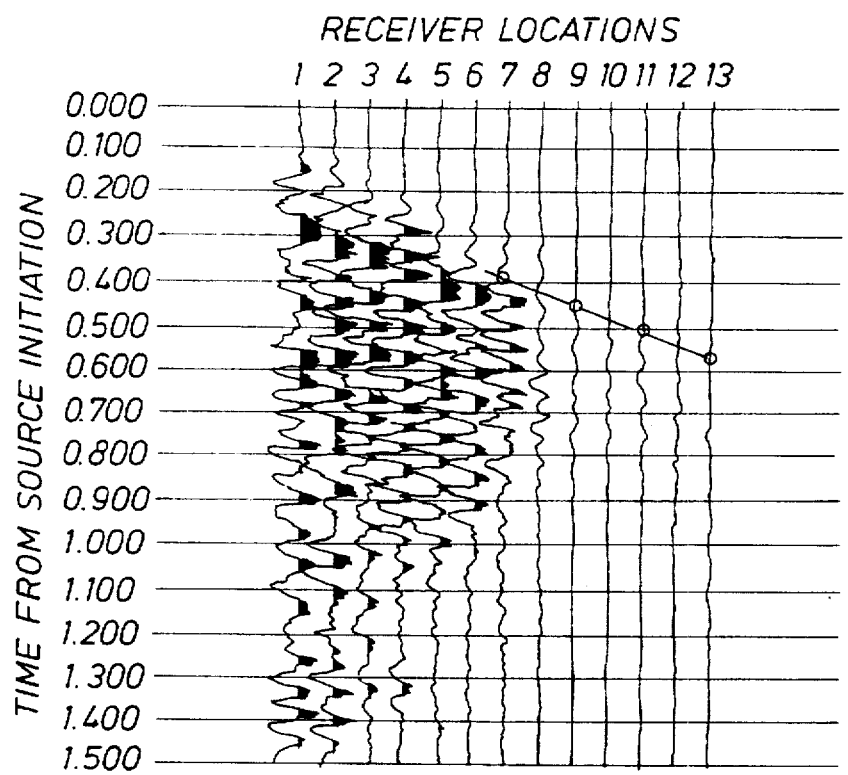

Now consider this same experiment if an anomalous perturbation is inserted into the physical model in the form of the low velocity scour zone. One could compare the scour zone to a lens being inserted into an otherwise uniform light field. Both the lens and the scour zone strongly perturb the distribution of energy in the resulting fields. Since the scour zone is a high impedance lens, its natural effect is to refract the elastic waves sharply at its boundaries. This effect is readily apparent when observing the data, shown in FIG. 6. The manifest effect is a strong change in recorded energy at the receivers at the bottom of the scour zone, (receiver 7 is at the same depth as the bottom of the scour zone). This observation is quantified by measuring the rms level of each receiver output and plotting it on FIG. 9. For the scour zone present model, the rms levels are the curve with the solid circles. This plot shows two effects, both predictable from general physical principals: (1) the scour filling material is highly absorptive, so the general recorded energy level is lower when the scour zone is present compared to the no-scour zone present experiment; and (2) the energy decay with increasing distance is strongly enhanced at the bottom of the scour zone. The recorded energy levels below the bottom of the scour zone are almost negligible compared to them above this boundary. The physical inference in the scour zone is acting as a strong lens diverting the energy to propagate horizontally, rather than vertically.

We can thus use the measure of rms energy as a function of depth to determine the depth of scour by associating the scour depth with the zone of accelerated energy decay. In a field situation, one would observe this anomalous energy decay zone slowly deepen with increased scour.

Figure 9:
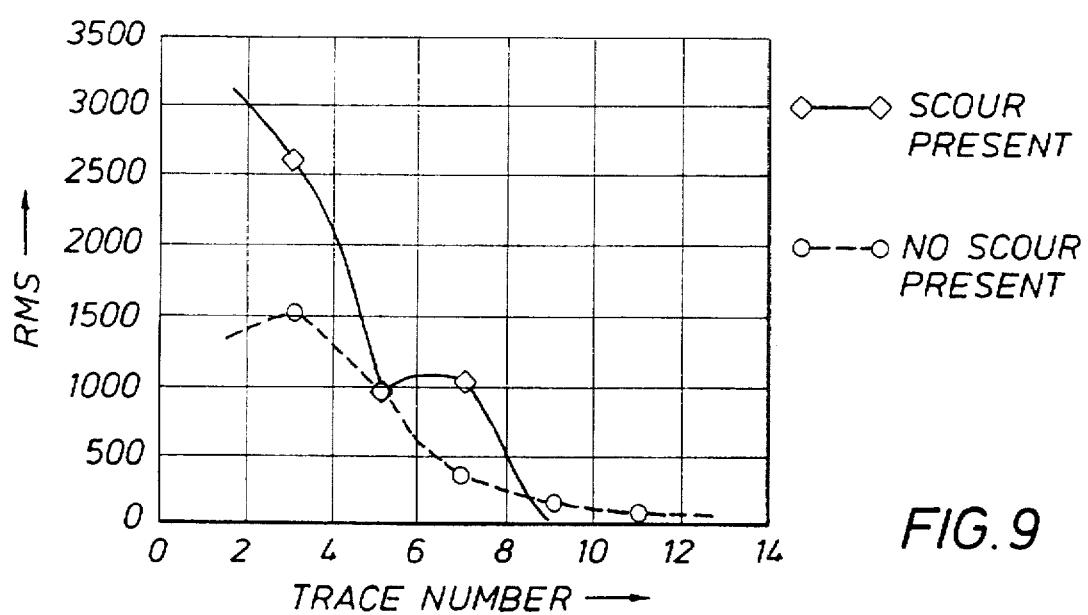
FIG. 9 shows root mean square, (rms) of the receiver power outputs.

With this arrangement, depth-of-scour can be measured by an accuracy limited by the interval between receivers in the buried pipe. The depth of the scour zone can be measured both from: (1) the depth at which the break in slope is observed in the direct arrival pattern; and (2) the depth where disruption in the refraction arrival pattern begins. These effects also are sketched in FIG. 4. The depth of scour also is coincident with a third indicator, the depth of the anomalous energy decay zone measured by the rms energy as a function of depth as shown in FIG. 9.

Figure 10B:
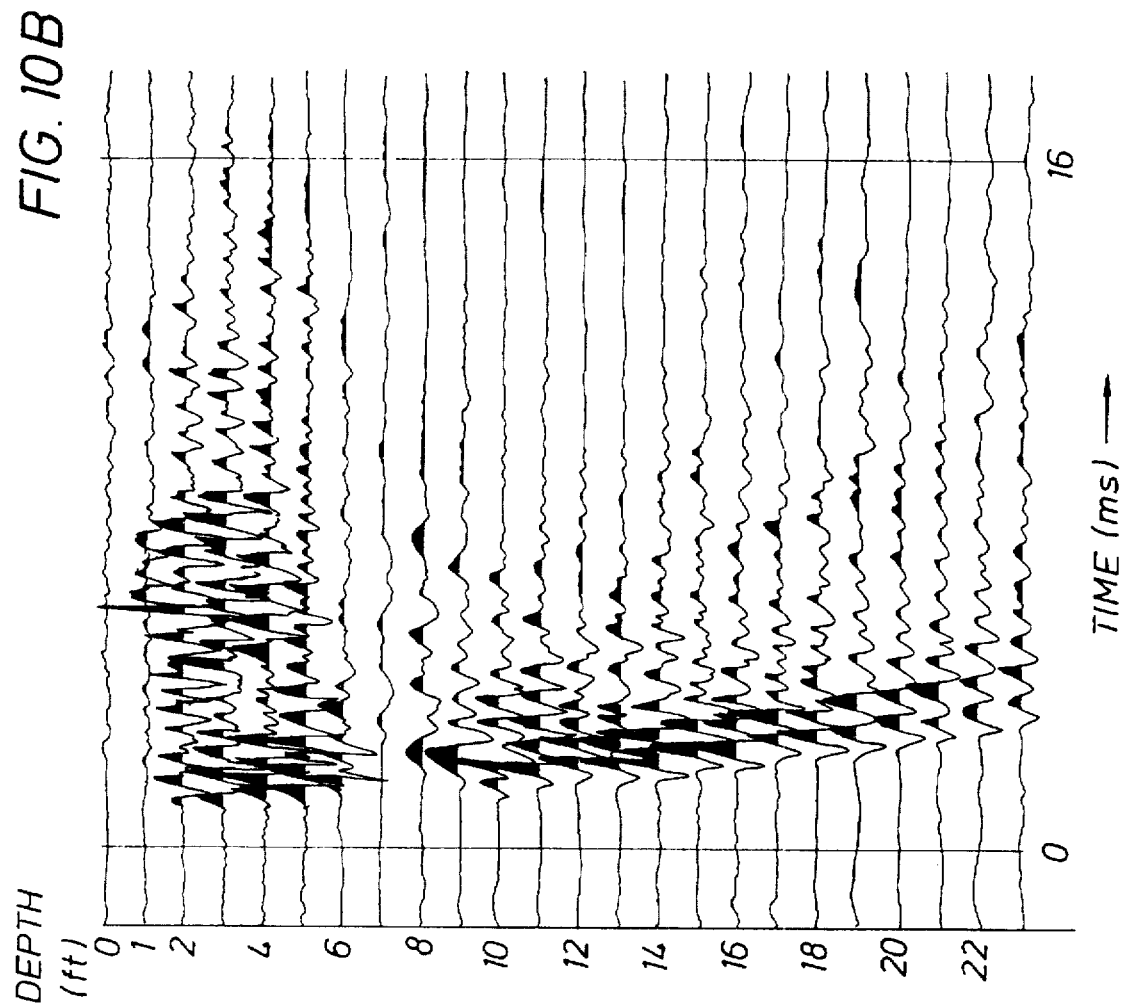
FIG. 10B is a plot of the elastic wave energy signals recorded through the receivers shown in FIG. 10A.
Figure 10A:
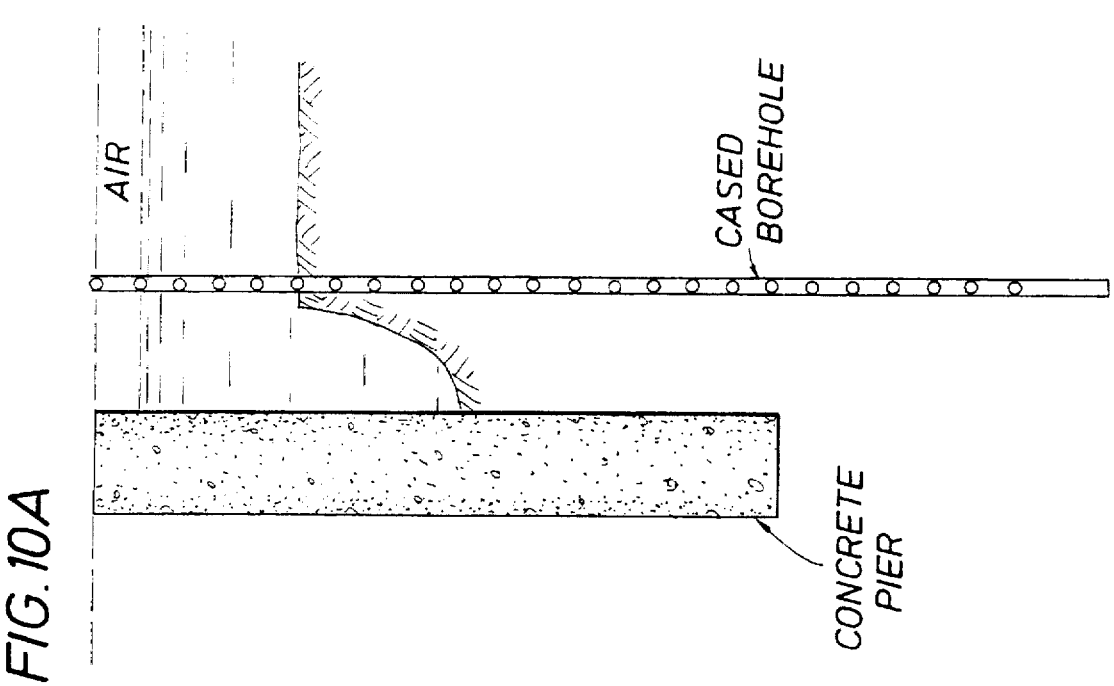
FIG. 10A is an elevational view of a concrete pier extending through a body of water into a scour zone and soil bottom, and an array of receivers, shown schematically, extending substantially vertically into the bottom.
Figure 11:
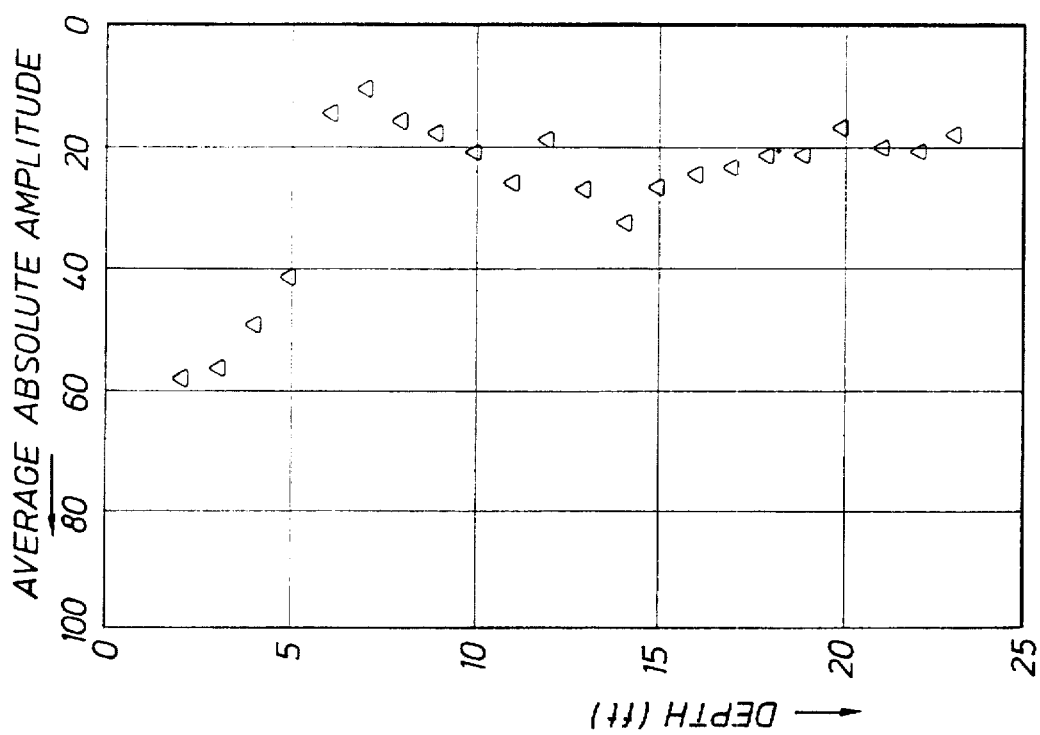
FIG. 11 is a plot of the Average Absolute Amplitudes of the signal data recorded through the receivers shown in FIG. 10A.

A fourth indicator is characterized by the data represented in FIGS. 10A, 10B and 11. FIGS. 10A and 10B show the geometry and seismic data of an experiment when the elastic energy source is a hammer striking the top of a pier. The elastic wave energy propagates down the pier and is refracted into the surrounding medium, where the energy crosses the zone between the pier and the receiver array to be recorded at the receiver sites, as shown in FIG. 10A. The resulting recorded data signals are shown in FIG. 10B.

Clearly, the data recorded at receiver locations 6, 7, 8, and 9, where the elastic energy passing through the scour zone is received, is substantially different in amplitude and pulse shape to the data representing the elastic energy waves that did not pass through the scour zone. This phenomena can be quantified in many ways, but FIG. 11 displays one method wherein Average Absolute Amplitude measurements quantify the appearance of the weak amplitudes at depths of six to ten feet. Other such computational methods for quantifying these characteristics include auto and cross correlation measurements of and between the signal data, and Fourier analysis of the data to calculate frequency and phase spectra.

When the Average Absolute Amplitude, or one of the other described calculation measurements, are made of the signal data and displayed for comparison as seen in FIG. 11, the boundaries and zones of anomalous behavior are easily recognized. Thus, in FIG. 11 the sharp break between the five and six foot depth readings is obvious, and corresponds physically to the water bottom interface with the soil. The anomalous behavior of the data ends at the ten to eleven foot level, which physically corresponds to the bottom of the soft, water-saturated mud occupying the scour zone laying on competent soil that has not been scoured out, as displayed in FIG. 10A.

A fifth indicator mentioned above, tube waves, may also be utilized to monitor the depth of a scour zone by measuring the onset depth of the waves at the changes in shear modulus associated with the scour interface. Thus, the onset scour depth can be monitored in real time during a flood to determine the rate and extent of scour. As the scour progresses, the onset depth of the tube waves will progressively deepen with the deepening of the scour zone-bottom soil interface. The strong water currents of a flood will often remove the soft mud from the scour zone leaving a clean, strong elastic modulus contrast boundary to generate the tube waves.

Figure 12:
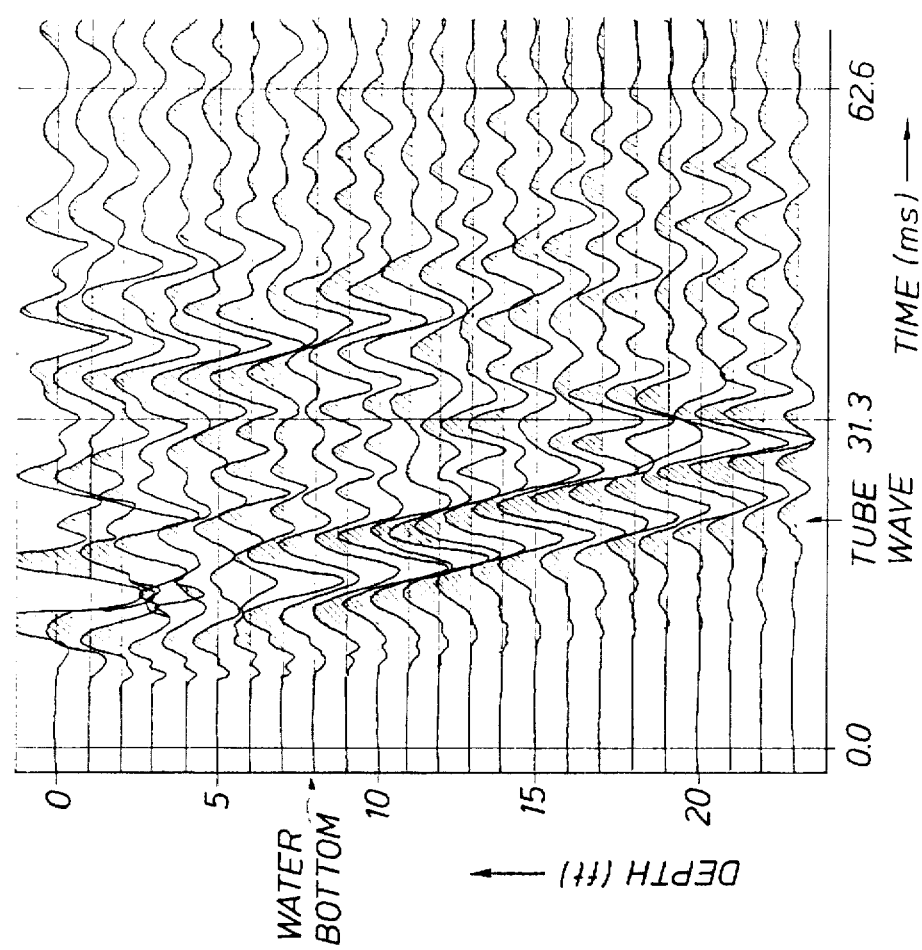
FIG. 12 is a plot of elastic wave signals initiated by tube waves.

FIG. 12 displays band-pass filtered seismic data obtained from an experiment with the elastic wave source offset three feet from a pier at a depth of two feet. The receiver array tube was positioned adjacent the pier and traversed a depth of approximately 25 feet. The bottom of the scour zone was observed to be in the 8 to 8.5 foot range, which is consistent with the coincidence of the tube wave initiation in FIG. 11. In actual practice, one would therefor look at the tube wave signals, in addition to the four criteria described above to make an assessment of depth of scour.

The receiver tube should be buried close enough to the pier or abutment or in a vertical hole in the pier or abutment where scour measurements are desired so that the direct arrival ray paths will traverse the developing scour zone, as sketched in FIGS. 3 and 10.

Accuracy of measuring depth-of-scour is controlled by the interval between receivers in the buried receiver pipe. A one foot interval is quite achievable, as the individual receivers are small.

Electrical cables and pneumatic hoses must be run to the receiver pipe and sound source. These cables and hoses are connected to the recording and control instruments and the air compressor. The recording and control instruments and air compressor can be easily packaged to fit inside a small trailer that can be parked on the bridge. If necessary, the cables and pneumatic hoses could be strung along the bridge to an off-bridge site.

The system has the capacity to compensate for increased noise levels expected during floods by:
  a. Increase the elastic wave source power by
    1. Increasing the gun size, and/or
    2. Increasing the pneumatic operating pressure level.
  b. Sum individual cycles of the experiment over longer time periods to obtain an $(N)^{1/2}$ signal-to-noise improvement, where N is the number of cycles summed. For example, since the system can be cycled up to two times per second, or 120 times per minute, a ten minute summing time range adds 1,200 cycles to give $(1200)^{1/2}=35:1$ signal-to-noise ratio improvement.

An additional advantage is that scour rates can be measured more accurately by placing the receivers closer together (say six inches apart). If the water flow characteristics were independently measured adjacent to the pier, some critical evaluation of empirical scour equations could be made.

The system would be easy to install during new bridge construction as the receiver array emplacement would be simplified. To install the system on existing bridges requires anchoring a core hole drilling barge adjacent to the pier, drilling (or washing) about a thirty foot hole into which the prebuilt receiver array is placed. In addition, instrument cabling must be run along the river bottom to the pier. This cabling must be armored and buried if debris or ice scour is expected at a specific site. To protect the receiver array from general scour damage, the receiver pipe can be shielded by first setting an H pile and placing the receiver pipe between the protecting flanges of the H pile. Alternatively, the receiver array can be located in a vertical hole in the pier or abutment as shown in FIG. 10.

The system has the cost advantage of only requiring the transducer receiver array to be permanently implanted at a bridge site. The sound source gun, recording and control instruments, air compressor, etc. can service multiple sites as they can be mounted in a portable trailer.

The system can be made vandal resistant by placing the electrical and pneumatic connection points at inaccessible places under the bridge span. The portable trailers can be made vandal proof by standard heavy construction and locking techniques, including automatic alarm systems.

The system can be highly automated by placing the recorder and gun instruments under program control by a microcomputer. The analysis of the data to measure depth-of-scour also can be computerized. When potentially dangerous scour conditions are sensed, the computer could activate a radio signal to a local center warning them of a scour alert. To build this automated system and define the values of the various parameters involved in the data analysis will require some test data to analyze.

In terms of maintenance, the computers, recorders, and elastic wave source systems have been highly developed for extended long life and ruggedness. They have been built for reliable operation in far more hostile environments than a trailer parked alongside a bridge, so maintenance should be relatively infrequent, and of the remove and replace subsystem type.

Modern data processing techniques were applied to the recorded data. Up to 200 repetitions of the experiment were summed at each placement of the source and receiver. Subsequent data processing techniques applied by computer to the digitized receiver signals were variable gain corrections as a function of source-receiver separation to compensate for spherical spreading; and bandpass filtering to improve the signal-to-noise ratio. In particular, low pass filtering suppressed the direct arrival relative to the refracted arrival and made timing the onset of the refracted event better. The data shown in FIGS. 5 and 6 were summed from 200 individual repetitions of the experiments, band pass filtered, and gain adjusted.

Verification that refracted signal has been recorded can be done by demonstrating that the extracted signals conform to theoretical travel times calculated from the minimum time paths defined by Snell's law. This is possible because the material elastic wave velocities and source-receiver geometry are known.

Figure 7:
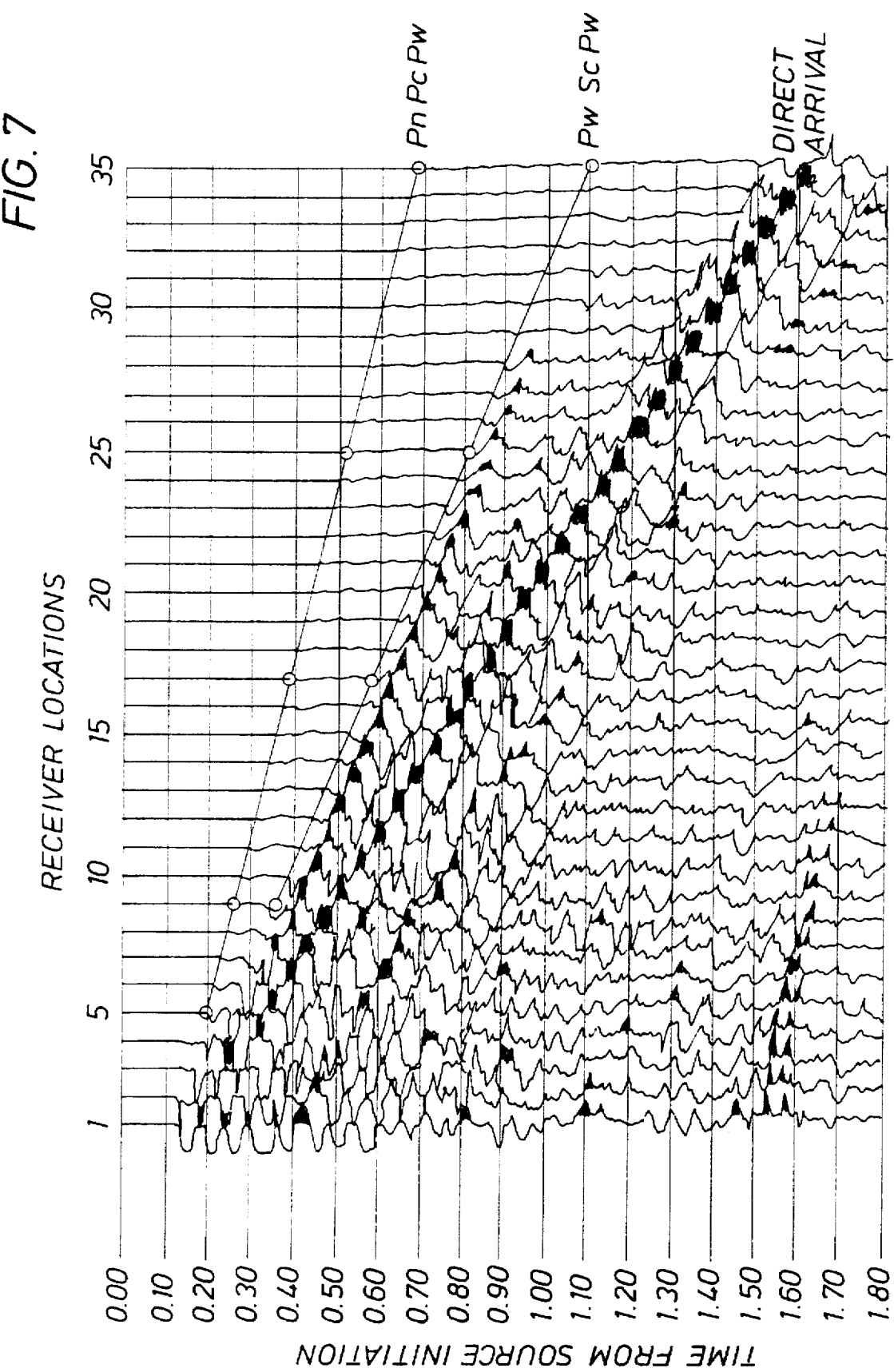
FIG. 7 is a data record of an offset test on cement slab.
Figure 8:
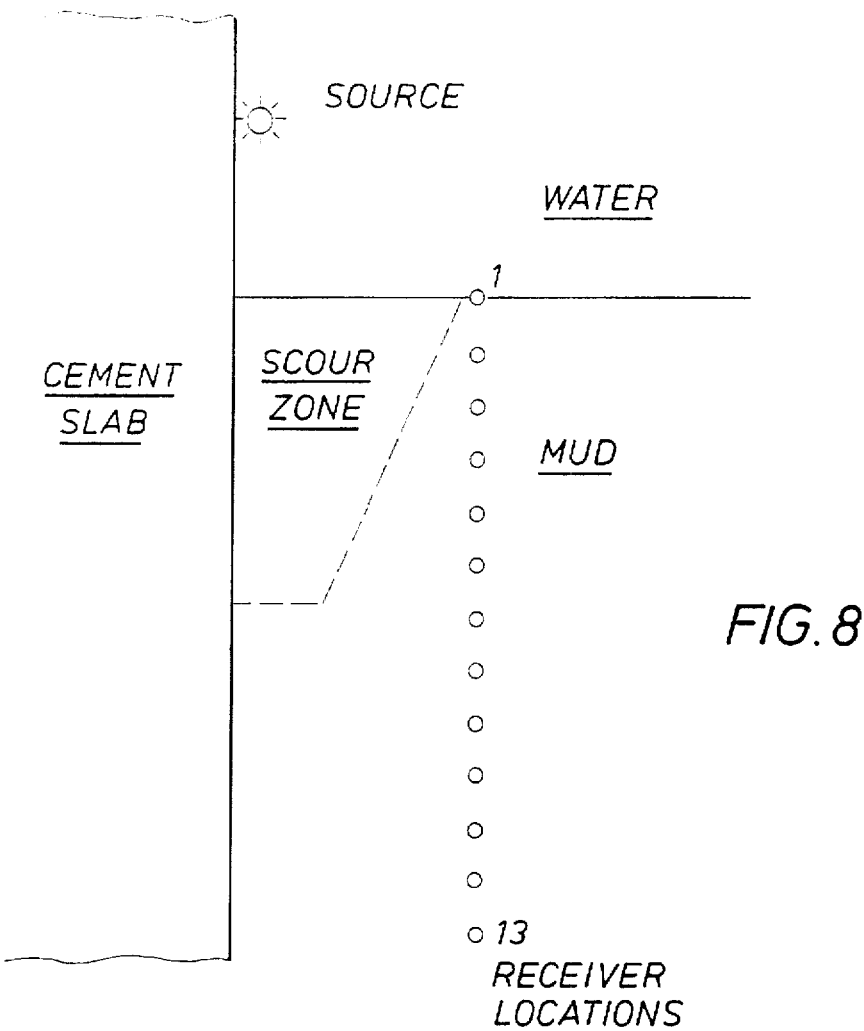
FIG. 8 is a schematic of the geometry of the test site.

Overlays of calculated travel times on the recorded data show the coincidence between recorded event and their theoretical travel times, which establishes their mode of propagation. This verification of the travel time calculations was done first on a model with only water overlying the cement slab. The data in FIG. 7 show the compression $(P_w P_c P_w)$ and shear $(P_w S_c P_w)$ refraction modes of propagation and the direct arrival. Note that the compression refraction, although the first arrival, as predicted by theory, is weaker than the shear refraction, which in turn is weaker than the direct arrival.

Figure 5:
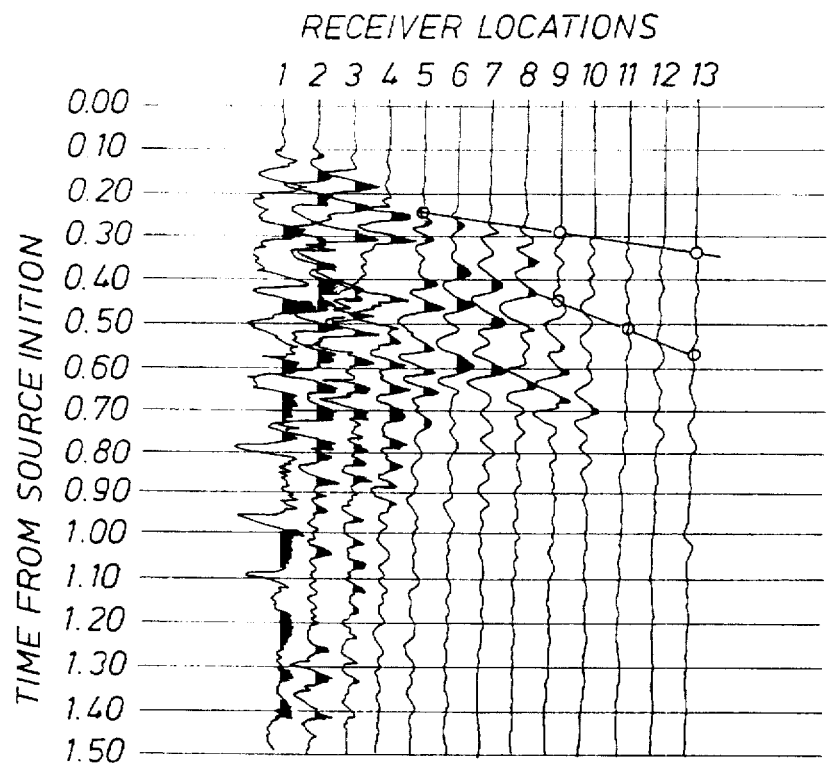
FIG. 5 and FIG. 6 are recorded traces of elastic waves reaching each receiver over a period of time without scour and with scour.

This verification technique was repeated on the more complex models with the cement slab buried in compacted sand, and both with and without a scour zone cut into the sand adjacent to the model pier. FIGS. 5 (no scour zone) and 6 (with scour zone) show these overlays. Analysis of the data shows that the strongest refraction event recorded is the shear refraction mode, rather than the compressional refraction mode. This is in agreement with other investigators (O'Brien, 1955). Other strong recorded events are the direct arrival and the Stoneley wave when only water overlays the slab. Both refraction modes radiate energy from the interface through the sand layer to the receivers. Only the shear refraction is strong enough to detect and use for scour detection. Even stronger (by a factor of 4 or more) is the direct arrival. Each can be used to identify changes in the soil characteristics adjacent to the pier by evaluating disruptions in the arrival times and rms energy levels received at the sequentially shallowest receivers relative to the deeper receivers. However, the data analysis differs depending on whether the direct arrival mode, or the shear refraction mode is used. It is also feasible to analyze both modes of energy from the same recorded data, as the system is linear and superposition applies. Consequently, this result does not limit the experimental technique at all, it only requires that the correct analysis technique be used on the appropriate data and provides additional robustness through redundancy of measurement.

A striking difference in overall appearance between FIGS. 5 (no scour zone) and 6 (scour zone present) is the abrupt change in recorded energy at the depth corresponding to the bottom of the scour zone (FIG. 6, receiver depth 7), when the scour zone is present. Contrast this to the smooth change in energy expected from spherical divergence and verified experimentally in FIG. 5, with no scour zone present. This characteristic is shown graphically in FIG. 9. This abrupt change in received energy as a function of depth is a powerful, easily measured diagnostic to indicate the depth of scour, particularly as one observes this transition progressively deepen with time at a fixed site.

The shear refraction event seen in FIG. 5 is difficult to recognize in FIG. 7.

Again, if one were to observe the progressive delay in direct arrival time, attenuation of repeatable refraction wave events, and abrupt changes in signal strength with depth, and these signal changes occurred in the predicted manner, then the conclusion could be made that scour and subsequent infilling with soft, high energy attenuating material was in progress. The depth of scour and infilling could be inferred from the depth to which these phenomena are observed.

From the foregoing it will be seen that this invention is one well adapted to attain all of the ends and objects hereinabove set forth, together with other advantages which are obvious and which are inherent to the method and apparatus.

It will be understood that certain features and subcombinations are of utility and may be employed without reference to other features and subcombinations. This is contemplated by and is within the scope of the claims.

Because many possible embodiments may be made of the invention without departing from the scope thereof, it is to be understood that all matter herein set forth or shown in the accompanying drawings is to be interpreted as illustrative and not in a limiting sense.

What is claimed is:

1. A method of measuring bottom scour adjacent a foundation structure extending into the bottom of a stream of flowing water, comprising the steps of:

positioning an array of elastic wave receivers in approximate vertical alignment so that a portion of the receivers will sense elastic waves that travel through the water above the scour, a portion will sense elastic waves that travel through the scour, and a portion will sense elastic waves that travel through the bottom adjacent the structure;

sending elastic waves from a single source through the water, the scour zone, and the bottom directly to the receivers and indirectly through the foundation structure to produce refracted signals that also travel to the receivers;

measuring the time for the direct and refracted signals to reach the receivers; and deducing the soil profile by using the known velocities of elastic waves in concrete, water, mud slurries, and soil to determine the amount of scour around the foundation structure.

2. The method of claim 1 wherein the elastic waves are transmitted from an elastic wave source positioned atop the foundation structure and the array of receivers is positioned adjacent to but spaced from the foundation structure.

3. The method of claim 1 wherein the elastic waves are transmitted from an elastic wave source attached to the side of the foundation structure.

4. The method of claim 1 wherein the elastic waves are transmitted from an elastic wave source positioned in the water adjacent the foundation structure.

5. The method of claim 1 wherein the array of receivers is located in an approximately vertical water filled hole in the foundation structure.

6. The method of claim 1 further including the step of positioning another approximately vertical array of receivers in an approximately vertical bore within the foundation structure.

7. A method of measuring bottom scour adjacent a foundation structure extending into the bottom of a stream of flowing water, comprising the steps of:

positioning an array of elastic wave receivers in a tube in approximate vertical alignment so that a portion of the receivers will sense elastic waves that travel through the water above the scour, a portion will sense elastic waves that travel through the scour, and a portion will sense elastic waves that travel through the bottom adjacent the structure;

sending elastic waves from a single source through the water, the scour zone, and the bottom directly to the receivers and indirectly through the foundation structure and the receiver array tube to produce refracted signals that also travel to the receivers;

measuring the time for the direct and refracted signals to reach the receivers;

measuring the onset depth of tube wave signals emanating from the receiver array tube using the receivers; and deducing the soil profile by using the known velocities of elastic waves in concrete, water, mud slurries, and soil, and the onset depth of the tube wave signals emanating from the receiver array tube to determine the amount of scour around the foundation structure.

8. The method of claim 1 wherein the soil profile is deduced by comparing the energies and frequency content of the signals measured at the receivers as a function of depth.

9. The method of claim 1 wherein the soil profile is deduced by comparing the root mean squares of the energies of the signals measured at the receivers as a function of depth.

10. The method of claim 1 wherein the soil profile is deduced by quantifying the measurement of weak signal amplitudes resulting from elastic energy waves that pass through the scour zone as a function of receiver depth.

11. The method of claim 10 wherein the weak signal amplitudes are quantified by calculating the average absolute amplitudes of the signals measured by the respective receivers.

* * * * *